(12) United States Patent
McKay

(10) Patent No.: US 8,790,677 B2
(45) Date of Patent: Jul. 29, 2014

(54) DEVICE AND METHOD FOR THE VACUUM INFUSION OF A POROUS MEDICAL IMPLANT

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1757 days.

(21) Appl. No.: 11/016,049

(22) Filed: Dec. 17, 2004

(65) Prior Publication Data

US 2006/0135938 A1 Jun. 22, 2006

(51) Int. Cl.
*A61F 13/00* (2006.01)

(52) U.S. Cl.
USPC .......................................................... 424/422

(58) Field of Classification Search
None
See application file for complete search history.

(56) References Cited

U.S. PATENT DOCUMENTS

| | | | |
|---|---|---|---|
| 4,294,250 A * | 10/1981 | Dennehey | 604/403 |
| 4,314,380 A | 2/1982 | Miyata et al. | |
| 4,748,070 A * | 5/1988 | Beehler | 428/198 |
| 4,937,194 A * | 6/1990 | Pattillo et al. | 141/10 |
| 4,976,731 A * | 12/1990 | Perry | 623/6.64 |
| 4,976,736 A | 12/1990 | White et al. | |
| 5,098,779 A | 3/1992 | Kranzler et al. | |
| 5,108,436 A | 4/1992 | Chu et al. | |
| 5,181,903 A | 1/1993 | Vann et al. | |
| 5,207,710 A | 5/1993 | Chu et al. | |
| 5,258,029 A | 11/1993 | Chu et al. | |
| 5,271,240 A * | 12/1993 | Detrick et al. | 62/268 |
| 5,290,494 A | 3/1994 | Coombes et al. | |
| 5,305,982 A * | 4/1994 | Tamari | 251/5 |
| 5,366,756 A * | 11/1994 | Chesterfield et al. | 427/2.26 |
| 5,397,572 A | 3/1995 | Coombes et al. | |
| 5,480,030 A * | 1/1996 | Sweeney et al. | 206/524.8 |
| 5,697,976 A | 12/1997 | Chesterfield et al. | |
| 5,746,317 A * | 5/1998 | Turner et al. | 206/423 |
| 5,769,897 A | 6/1998 | Harle | |
| 5,932,256 A * | 8/1999 | Mandish | 425/405.1 |
| 6,009,603 A * | 1/2000 | Gallagher | 24/585.12 |
| 6,013,853 A | 1/2000 | Athanasiou et al. | |
| 6,063,117 A | 5/2000 | Perry | |
| 6,138,711 A * | 10/2000 | Lung-Po | 137/527.8 |
| 6,161,695 A * | 12/2000 | Nicolais | 206/438 |
| 6,180,606 B1 | 1/2001 | Chen et al. | |
| 6,559,244 B1 * | 5/2003 | Meinander et al. | 525/420 |
| 6,592,260 B1 * | 7/2003 | Randall et al. | 383/64 |
| 6,773,425 B1 * | 8/2004 | Tamari | 604/403 |
| 2002/0088201 A1 * | 7/2002 | Siccardi | 53/131.5 |

FOREIGN PATENT DOCUMENTS

| EP | 0 398 497 | 11/1990 |
|---|---|---|
| EP | 0 928 612 | 7/1999 |

OTHER PUBLICATIONS

Noah et al. Impact of sterilization on the porous design and cell behavior in collagen sponges prepared for tissue engineering. Biomaterials 2002 23:2855-2861.*
Itokazu et al. Biomaterials 1998 19:817-819.*
Engh et al. Journal of Bone and Joint Surgery 1987 69B:45-55.*

* cited by examiner

*Primary Examiner* — Juliet Switzer
*Assistant Examiner* — Caralynne Helm
(74) *Attorney, Agent, or Firm* — Sorell Lenna & Schmidt LLP

(57) ABSTRACT

Disclosed is a novel device for the vacuum infusion of a porous medical implant contained therein with one or more pharmaceutical substances and a method for the device's use. The device is deformable, and capable of adjusting to the outer contour of a porous medical implant to facilitate packaging, shipping and storage of the implant contained within the device. In addition, the device is unbreakable, easily disposed of after use, maintains the implant in a sterile condition before and after infusion and minimizes the quantity of pharmaceutical substance needed for infusion. Use of the device provides for rapid and complete infusion of a variety of pharmaceutical substances into a porous implant prior to surgery.

20 Claims, 4 Drawing Sheets

DEVICE AND METHOD FOR THE VACUUM INFUSION OF A POROUS MEDICAL IMPLANT

BACKGROUND OF THE INVENTION

Porous medical implants are commonly infused with a variety of pharmaceutical substances including osteoinductive and nutritional factors, drugs, antimicrobial agents, calcium containing compounds, blood proteins and related materials; and growth factors to facilitate the implant's incorporation within the body and avoid unwanted complications resulting from surgery or the condition being treated. The infusion of substances into established materials such as collagen sponges is rapid upon contact with a solution or dispersion of the pharmaceutical substance. However, many of the newer load bearing materials, such as porous calcium phosphate ceramic, absorb pharmaceutical substances slowly and incompletely.

A number of techniques have been employed to eliminate gases from a porous implant and improve infusion of a variety of materials therein. U.S. Pat. No. 5,181,903 (Vann, et al.) issued on Jan. 26, 1993, discloses a method for eliminating undissolved gases and the incorporation of therapeutic agents into a biomaterial utilizing hydrostatic pressure. Prior to the application of pressure, the solution containing the therapeutic agent and optionally the biomaterials are degassed at reduced pressure, the biomaterial is submerged in the therapeutic agent and hydrostatic pressure is applied to all surfaces of the biomaterial.

U.S. Pat. No. 6,063,117 (Perry) issued on May 16, 2000, discloses a non-polyethylene orbital implant that can comprise a porous ceramic material and a method for infusing either gentamicin or a fibroblast growth factor prior to implantation. The implant was placed in a sterile 30 mL syringe, filled with enough solution to immerse the implant, the syringe capped and the plunger withdrawn to create a mild vacuum. Residual air was released upon slight agitation of the syringe barrel and by continued contact with the solution overnight at 4° C.

U.S. Pat. No. 5,769,897 (Harle) issued on Jun. 23, 1998, discloses a vacuum vessel that can be utilized for treating, storing and transporting an artificial bone material. The vessel disclosed is constructed of a rigid plastic, has an opening for insertion of the bone material, a lid to close and seal the opening and has two ports, one for connecting to a vacuum source and the other sealed with a self-sealing rubber membrane for the introduction of a pharmaceutical substance.

In spite of these advances, the need exists for an improved device for storing, transporting and infusing a porous implant and a method for the improved device's use.

SUMMARY OF THE INVENTION

One object of the present invention is to provide a novel deformable vacuum infusion device suitable for packaging and for rapid and complete vacuum infusion of a liquid, typically a saline solution or a solution of a pharmaceutical substance, into a porous medical implant. Preferred embodiments of the device provides an environment wherein a sterile implant sealed within the device at manufacture or thereafter remains sterile, can be infused prior to surgery with a minimal quantity of one or more pharmaceutical substances and can be maintained in its sterile condition until implanted.

In addition, because of the preferred device's lightweight construction and ability to approximately conform to the approximate shape of the implant, packaging, shipping and storage of the implant and device is facilitated. Finally, the preferred device's design and materials of construction facilitate removal of the implant from the device and disposal of the used device by standard methods.

In one aspect of the present invention a device for vacuum infusion of one or more pharmaceutical substances into a porous medical implant is provided, the device comprising: a deformable pouch constructed from a biocompatible material, the pouch containing the porous medical implant and having an orifice suitable for the introduction of the pharmaceutical substance and an orifice suitable for connecting to a vacuum. A single multifunctional orifice can be provided for both the introduction of the pharmaceutical substance and for connecting to a vacuum or multiple orifices can be provided having task specific designs. In a second aspect of the present invention a device is provided for vacuum infusion of a pharmaceutical substance into a porous medical implant, the device comprising a deformable pouch having a volume between about 1 to about 20 cubic centimeters constructed from a biocompatible material, the pouch having at least two orifices; the first orifice having an open condition suitable for receiving a porous medical implant and suitable for subsequent closure; the second orifice having a coupling member suitable for the introduction of a pharmaceutical substance and for connecting to a vacuum.

It is a further object of this invention to provide a method utilizing the novel device to vacuum infuse medical implants with solutions of saline or pharmaceutical substances prior to implantation. In one aspect of the present invention a method is provided for infusing a porous medical implant with one or more pharmaceutical substances, the method comprising providing a porous medical implant sealed within a deformable pouch, the pouch constructed from a biocompatible material; contacting the implant with a pharmaceutical substance; causing the pressure within the sealed pouch to be reduced to less than the pouch's external pressure and maintaining this reduced pressure condition until a desired level of infusion has been accomplished. Utilization of this method for the infusion of pharmaceutical substances into a porous medical implant maintains the implant's sterile condition from manufacture to implantation, provides for rapid and complete infusion utilizing a minimum quantity of pharmaceutical substance and allows the infused implant to remain infused, sterile and ready for implantation until needed.

It is still a further object of this invention to provide a porous medical implant infused with a pharmaceutical substance according to the novel method of this invention. In one aspect of the present invention, porous implants infused to a desired level with pharmaceutical substances to facilitate incorporation into the body are available to the surgeon as needed in a convenient form and in a sterile condition.

Related objects and advantages of the present invention will be apparent from the following description.

DESCRIPTION OF THE PREFERRED EMBODIMENTS

Figure 1:
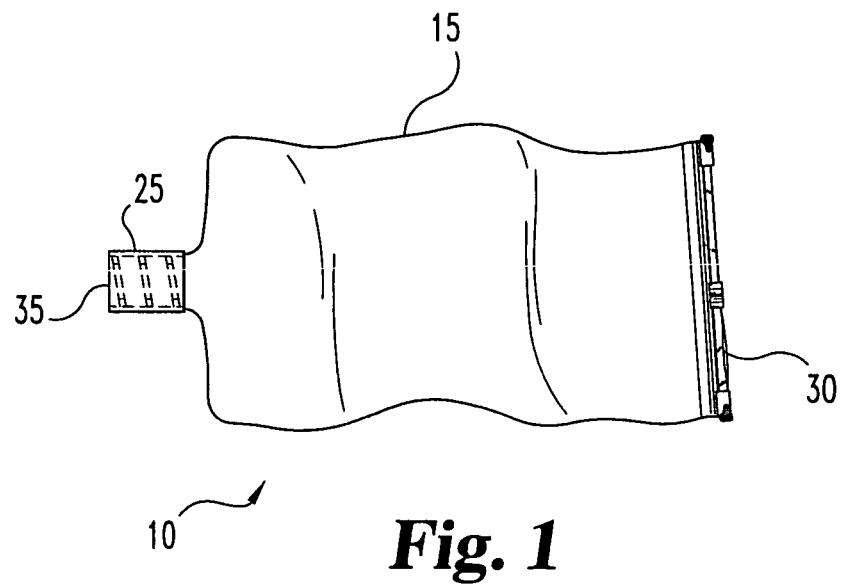
FIG. 1 is a front elevation view of a device for vacuum infusion of a pharmaceutical substance into a porous medical implant.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
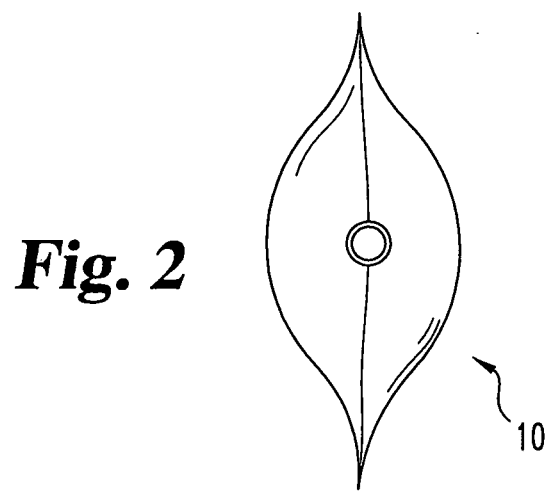
FIG. 2 is an end elevation view of the device.

In the illustrated embodiment of the present invention there is provided a medical device for conveniently storing, transporting and infusing a porous medical implant with one or more pharmaceutical substances, the infusion occurring at reduced pressure prior to surgery. Preferred embodiments of the device are deformable, unbreakable, lightweight and constructed of inexpensive and readily available material. The preferred device is capable of maintaining a porous implant sealed therein in a sterile condition from the implant's manufacture until its removal for implantation and in a surgical environment provides for its rapid and complete infusion as required. There are shown in FIGS. 1 and 2 views of the device 10 comprising a deformable pouch 15 constructed from a biocompatible material. The pouch 15 has a first orifice 30 suitable in an open condition for receiving a porous medical implant and capable of being sealed thereafter and a second orifice 35. The second orifice 35 is fitted with a coupling member 25 suitable for the introduction of a pharmaceutical substance, for connection to a vacuum, and for closing orifice 35 to maintain a sterile internal environment. Preferred devices have a neck 27 (FIG. 3) having either sufficient thickness to prevent its collapse under vacuum or a rigid insert therein.

Preferred materials of construction for the flexible pouch include any flexible biocompatible material sufficiently non-porous to prevent entry of microorganisms through its surface and to support the reduced pressures utilized for the infusion process. Preferred biocompatible materials include, but are not limited to polyethylene, polypropylene, polyurethane, an biodegradable poly-fibers such as for example polylactic acid and polyglycolic acid.

The biocompatible material's thickness can vary according to the reduced pressure required for the infusion process the material's strength and its flexibility. The appropriate thickness for the material can readily be determined by one of ordinary skill in the art without undue experimentation. Preferred devices are generally constructed from biocompatible materials having a thickness from about 0.001 inch to about 0.012 inch and more preferred devices are constructed from materials having a thickness from about 0.002 inch to about 0.008 inch. Although the biocompatible material utilized to manufacture the device can be transparent, semi-transparent or opaque, transparent or semi-transparent materials allow the infusion process to be followed visually and are preferred.

The coupling member 25 can be of any design suitable for the addition of the pharmaceutical substance and for connecting to a vacuum source. Preferred devices illustrated in FIGS. 1, 3-7 have a single coupling member 25 for making connections through which the additions of one or more pharmaceutical substances can be made and through which the device can be evacuated. The coupling member 25 can simply provide for connections that allow for the necessary additions and allow for the connection to a vacuum system as illustrated in FIGS. 1-4 or can alternatively include a valve 29, as illustrated in FIG. 6 that will allow the device and its contents to be evacuated and sealed to retain a reduced pressure therein or sealed at atmospheric pressure to maintain a sterile internal environment. Alternatively, the device can be provided with additional ports for additions or evacuation by: (1) adding one or more additional orifices and/or coupling members, (2) by the incorporation of a manifold system into the coupling member, or (3) by connecting coupling member 25 to an external manifold system. For preferred embodiments of device 10, coupling member 25 is a union having either internal or external threads. A particularly preferred coupling member is a luer lock connection of the type used on syringes. A preferred coupling member 25 is capable of accepting a closure 55 (FIGS. 3 and 4) or otherwise closing orifice 35 such as through a valve 29 (FIG. 6) to maintain a sterile internal environment. Closure 55 can be removed to add a pharmaceutical substance, to connect device 10 to a vacuum source, or to connect device 10 to an external manifold providing connections to a source of the pharmaceutical substance and the vacuum. Additionally, orifice 35 may be fitted with a self-sealing semi-permeable membrane 17 (FIG. 4) through which the pharmaceutical substance can be added utilizing a syringe. Upon connecting to a vacuum source 50 (FIG. 5) the membrane provides for the evacuation of gases from the device, but ensures that no liquid is evacuated.

The volume of device 10 must be sufficiently large to contain the porous implant 20 (FIG. 3) and the pharmaceutical substance. Generally the device is sized slightly larger than the implant to facilitate placement of the implant therein. Typical devices will have a volume between about 1 and about 20 cubic centimeters, more preferred volumes ranging between about 4 and about 10 cubic centimeters.

Figure 3:
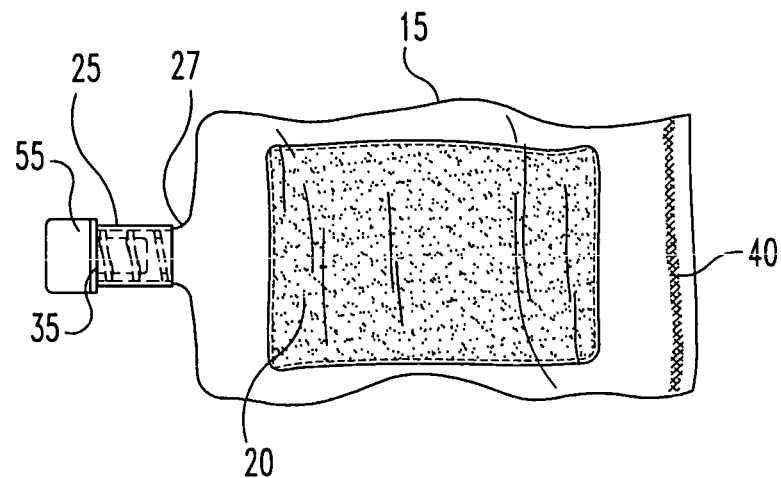
FIG. 3 is an elevation view of the device including a porous medical implant sealed therein.

Shown in FIG. 3 is a view of the medical device 10 containing a porous medical implant 20 sealed therein by a sealed region 40, resulting from a heat sealing process or the application of a biocompatible adhesive. The device 10 can also be fitted with a quick closure such as for example a zip-lock mechanism as illustrated in FIG. 1. For devices in which a sterile porous implant 20 is sealed within the device 10 at a manufacturing facility, a closure resulting from a heat sealing process is preferred. However, when the implant 20 is to be added to device 10 at a later time, as for example in a hospital or surgical environment, then the alternative methods of closure provide advantages. Closure 55 (FIG. 3) or valve 29 (FIG. 6) seals the implant within the device and maintains the implant's sterile condition.

Although the infusion of any porous medical implant can benefit from the advantages of device 10 and vacuum infusion, porous medical implants constructed from materials that infuse slowly under ambient conditions primarily benefit from the device's use. Preferred materials of construction for porous implants utilized in this invention include calcium phosphate ceramics, porous metals, ceramic polymer composites, human allografts, cadaver bones and porous polymers. Ceramic polymer composites include, but are not limited to, calcium phosphate composites with degradable polymers such as for example polylactic acid or polyglycolic acid. Porous implants constructed of a calcium phosphate ceramic are most preferred. The porous implants constructed from these materials can include, but are not limited to load-bearing interbody constructs and cranial and dental implants.

Figure 4:
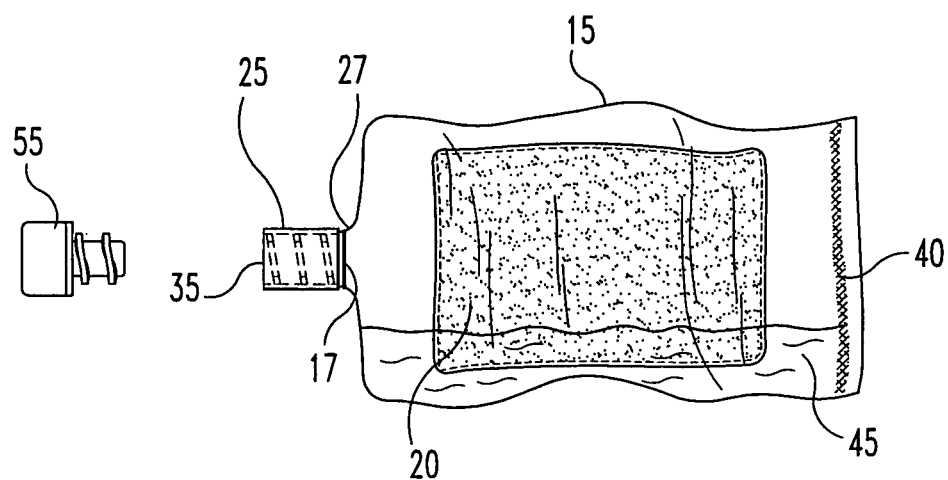
FIG. 4 is an elevation view of the device including a porous medical implant and a pharmaceutical substance contained therein.

Shown in FIG. 4 is a view of the medical device 10 containing a porous medical implant 20 and a pharmaceutical substance 45 sealed therein by a sealed region 40, resulting from a heat sealing process. A wide variety of pharmaceutical substances are typically infused into porous implants prior to implantation. General types of pharmaceutical substances include, but are not limited to osteoinductive factors, growth factors, nutrients, drugs, antimicrobial agents, calcium containing compounds, blood proteins and other products that enhance healing or bone repair. Examples of osteoinductive factors include, but are not limited to demineralized bone particles, Bone Morphogenetic Proteins (BMPs), and other factors such as extracts of demineralized bone matrix. Specific examples of BMPs include, but are not limited to BMP2, BMP-7, BMP-2a, BMP-4, BMP-5, BMP-6, and BMP-8. Examples of growth factors include, but are not limited to Growth Differentiation Factors (GDF) such as GDF-5, 6, and 7, Demineralized Bone (DBM) solution, Chrysalin, Transforming Growth Factor-Beta (TGF-$\beta$) such as TGF-$\beta$1, TGF-$\beta$2, and TGF-$\beta$3, Transforming Growth Factor-Alpha (TGF-$\alpha$), Epidermal Growth Factor (EGF), Insulin Like Growth Factor-I or II, Interleukin-I (IL-I), Interferon, Tumor Necrosis Factor, Fiberblast Growth Factor (FGF), Platelet Derived Growth Factor (PDGF), Nerve Growth Factor (NGF), and other materials that exhibit growth factor or growth factor-like effects. Examples of nutrient factors include, but are not limited to, vitamins, hormones, individual or combinations of amino acids, carbohydrates or derivatives thereof, fats or derivatives thereof, alcohols or derivatives thereof, inorganic salts, and trace elements. Examples of drugs include, but are not limited to, tetracycline, antimicrobial agents such as chlorahexadine or zinc citrate, anti-inflammatory agents such as steroidal or nonsteroidal agents as for example flurbiprofen. Blood products include, but are not limited to fibrin, fibronectin, clotting factors, and Plasma Rich Plasma (PRP). Calcium compounds include, but are not limited to calcium hydroxide, calcium lactate and other inorganic or organic calcium salts.

Although preferred pharmaceutical substances 45 are typically infused as an aqueous solution, an aqueous suspension or an emulsion, a dehydrated form of the pharmaceutical substance can be packaged with the implant or added to device 10 and hydrated or dissolved prior to implantation. Hydration or dissolution in a solvent can be accomplished by the further addition of a solvent such as water to the device containing the implant and dehydrated form of the pharmaceutical substance prior to infusion. The concentration of the pharmaceutical substance 45 utilized varies depending on the identity of the substance, its solubility and the device being infused. For BMP, concentrations of 0.1 to 4 mg/mL have proven useful. Similarly, the amount of pharmaceutical substance 45 to be infused can similarly vary. The determination of the optimum concentration and total loading of the pharmaceutical substance can readily be determined by one of ordinary skill in the art without undue experimentation.

Figure 5:
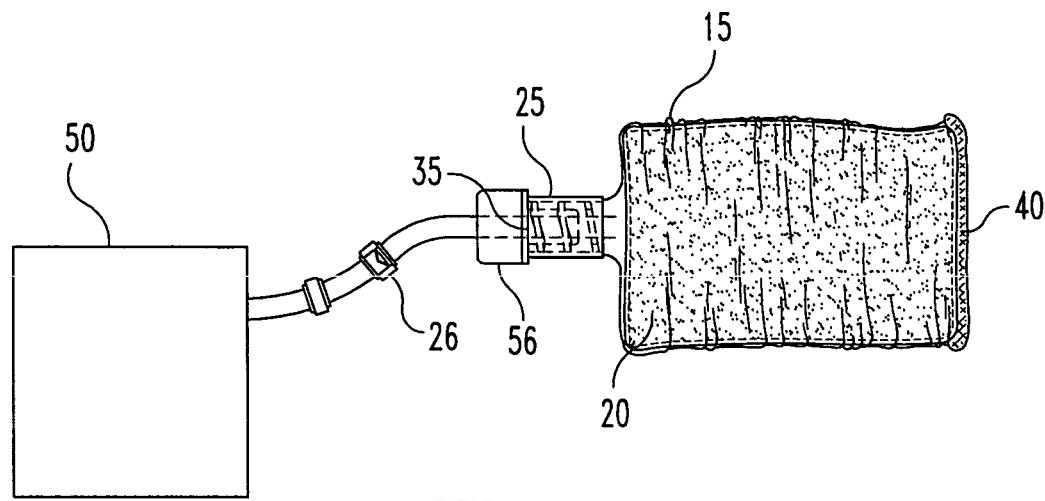
FIG. 5 is an elevation view of the device including a porous medical implant sealed therein and connected to a vacuum source at reduced pressure.
Figure 6:
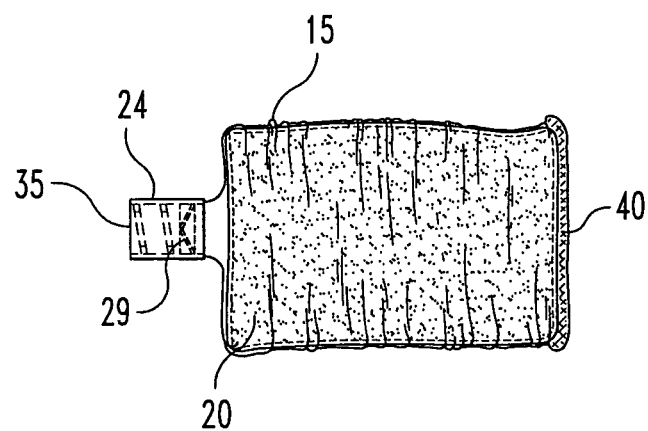
FIG. 6 is an elevation view of the device including a porous medical implant infused and sealed therein wherein the device and its contents have an internal pressure of less than the external pressure.

Shown in FIG. 5 is a view of device 10 connected to vacuum source 50 through connector 56 inserted into coupling member 25, device 10 containing a porous medical implant 20 infused with a pharmaceutical substance 45 (FIG. 4), the device and its contents being maintained at reduced pressure. During infusion the pressure inside the device is reduced, air is evacuated from device 10 and porous implant 20; the deformable pouch 15 contracts and conforms to the shape of implant 20 and the pharmaceutical substance 45 is forced into implant 20. Although not required, complete infusion is accomplished when a volume of pharmaceutical substance corresponding to the pore volume of the porous implant 20, has been adsorbed. A deformable pouch 15 made from transparent or semi-transparent biocompatible material is preferred in order to provide a visual determination of the progress of infusion by the disappearance of the pharmaceutical substance.

Another feature of this invention is the method for infusing a porous medical implant with one or more pharmaceutical substances. Although infusion can be carried out any time prior to surgery, infusion just prior to surgery is preferred. A pharmaceutical substance 45 is added to the device 10 through coupling member 25. For preferred devices utilizing a luer lock for its coupling device, addition can be carried out with a syringe fitted with a luer lock connector and containing a solution of the pharmaceutical substance upon removal of closure 55 and attachment to the luer lock. After addition of the pharmaceutical substance, a vacuum source 50 (FIG. 5) is attached to coupling member 25 and the pressure inside of device 10 is reduced. Infusion can take place over a wide range of temperatures and pressures. Generally, infusion will occur at faster rates at lower internal pressures and higher temperatures. Preferred pressures for infusion are below about 500 mmhg, or generally from about 10 mmhg to about 500 mmhg, and more preferred pressures are below about 300 mmhg, or generally from about 50 mmhg to about 300 mmhg. The infusion temperature can be controlled by any know method of heat transfer that doesn't affect the integrity of the device 10, or adversely affect the pharmaceutical substance or the implant 20. Preferred methods of controlling the infusion temperature include, but are not limited to immersing the device in a fluid, including air, maintained at the desired temperature or exposing the device 10 and its contents to infra-red radiation. Preferred infusion temperatures will be between about ambient to 37° C.

Pharmaceutical substance 45 can also be added after device 10 and its contents have been connected to vacuum source 50 and evacuated, provided means are available to maintain device 10 and its contents at a desired pressure throughout the addition of pharmaceutical substance and the remaining infusion process. This can be accomplished by utilizing: (1) a coupling member 24 having a valve 29 incorporated therein as illustrated in FIG. 6; (2) a valve 26 separate from coupling member 25 but connected in series between the vacuum source and the coupling member as illustrated in FIG. 5; or (3) a manifold system having one or more valves capable of providing two or more additional ports access to orifice 35. The manifold can be utilized to connect the vacuum source to device 10 through a first port having access to orifice 35 and establish an appropriate pressure therein. While maintaining the pressure, manipulation of a valve of the manifold can cause orifice 35 to be disconnected from the first port and connected to a second port through which a pharmaceutical substance can be added. Similarly a valve 26 in its open position having access to orifice 35 can be utilized to connect the vacuum source 50 to device 10 and establish an appropriate pressure therein. Closure of valve 26 maintains the reduced pressure within device 10 while the connection to vacuum source 50 is severed and a connection is made with a source of the pharmaceutical substance(s). Upon opening the valve, the pharmaceutical substance(s) is drawn into device 10. Following addition of the pharmaceutical substance(s)

and closure of valve 26, a connection with vacuum source 50 can be re-established if needed or desired.

Figure 7:
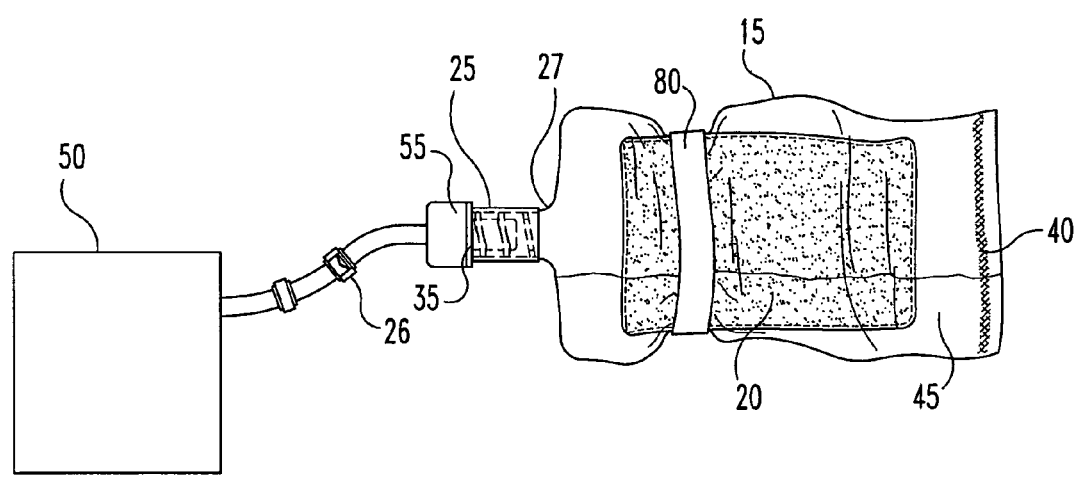
FIG. 7 is an elevation view of the device including a porous medical implant and a solution containing a pharmaceutical substance contained therein wherein the device is fitted with a member capable of conforming the exterior of the device to the circumference of the porous medical implant.

Shown in FIG. 7 is an embodiment of preferred device 10 fitted with a member 80. Member 80 is capable of conforming to the exterior of pouch 15 about a circumference of the porous implant to form at least a partial seal between 15 and 20. Although the member can be located at any position along a circumference of the implant, a preferred location is in the vicinity of a coupling member through which the vacuum 50 is connected.

Upon the creation of a pressure differential between the device's interior and exterior by, for example, connecting a vacuum source 50 to coupling member 25, the at least partial seal formed by member 80 forces liquid to be pulled into the implant facilitating the infusion process.

Member 80 can be a narrow band, a wide band that extends across the length of the implant or have any width between. Member 80 can be constructed of a natural or synthetic rubber or plastic, constructed from a rigid material capable of assuming and maintaining a close fit about device 10 and a circumference of porous implant 15 or be an integral part of device 10.

In another aspect of the present invention, novel infused porous medical implants are provided that have been infused with a pharmaceutical substance according to the procedure described above. Pharmaceutical substances infused include, but are not limited to, osteoinductive factors, growth factors, nutrients, drugs, antimicrobial agents, calcium containing compounds, blood proteins and other products that enhance healing or bone repair. Preferred infused porous implants are made from a calcium phosphate ceramic; calcium phosphate composites with polymers, particularly biodegradable polymers such as polylactic acid or polyglycolic acid; ceramic polymer composites; porous polymers; human allografts; cadaver bone and porous metals. More preferred infused porous implants are made from a calcium phosphate ceramic.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A device for the infusion of a liquid into a porous medical implant at reduced pressure, the device comprising:
   a deformable pouch with an interior surface,
   a sterile porous medical implant that is sealed within the interior of the pouch by heat-sealing or by a biocompatible adhesive, and
   a band member conforming to the exterior of the pouch about a circumference of the porous medical implant and capable of forming at least a partial seal between the pouch and the implant;
   wherein the pouch is constructed of a biocompatible material comprising a biodegradable polymer and its interior is sterile;
   wherein the pouch comprises a multifunctional orifice suitable for the introduction of the liquid and for connecting to a vacuum, said multifunctional orifice is fitted with a self-sealing, semi-permeable membrane configured to permit the passage of gases and resist the passage of liquids, said multifunctional orifice is further fitted with a coupling member comprising an inner surface defining a passageway as well as a valve that is disposed entirely within the passageway, wherein the valve comprises an open position for evacuating the interior of the pouch or drawing liquid into the interior of the pouch and a closed position for maintaining a reduced internal pressure; and
   wherein the internal surface of the pouch contacts and is configured to conform to the entire exterior surface of the porous medical implant when pressure is reduced in the interior of the pouch so as to allow infusion of the liquid into the porous medical implant when the liquid is introduced into the interior of the pouch.

2. The device of claim 1, wherein the coupling member is a threaded union.

3. The device of claim 2, wherein the threaded union is a luer lock.

4. The device of claim 2, wherein the biocompatible material is selected from the group consisting of polylactic acid and polyglycolic acid.

5. The device of claim 4, wherein the biocompatible material has a thickness of between 0.002 and 0.008 of an inch.

6. The device of claim 4, wherein the porous medical implant is constructed from a porous material selected from the group consisting of calcium phosphate ceramics, porous metals, ceramic polymer composites, human allografts, cadaver bones and porous polymers.

7. The device of claim 6, wherein the porous material is a calcium phosphate ceramic.

8. The device of claim 2, further comprising a liquid that includes pharmaceutical substance.

9. The device of claim 8, wherein the pharmaceutical substance is selected from the group consisting of osteoinductive factors, growth factors, nutrients, drugs, antimicrobial agents, calcium containing compounds and blood proteins.

10. A device for vacuum infusion of a liquid into a porous medical implant, the device comprising:
    a deformable pouch having a volume between 0.061 to 1.220 cubic inches that has a sterile interior surface and is constructed from a biocompatible material comprising a biodegradable polymer, the pouch comprises:
    a first orifice that is suitable for receiving a porous medical implant;
    a second orifice adapted for the introduction of the liquid and for connecting to a vacuum, wherein the second orifice is fitted with a self-sealing, semi-permeable membrane configured to permit the passage of gases and resist the passage of liquids, said second orifice is further fitted with a coupling member comprising an inner surface defining a passageway as well as a valve that is disposed entirely within the passageway, wherein the valve comprises an open position for evacuating the interior of the pouch or drawing liquid into the interior of the pouch and a closed position for maintaining a reduced internal pressure;
    a sterile porous medical implant having an exterior surface, wherein the interior surface of the pouch contacts and is configured to conform to the entire exterior surface of the porous medical implant when pressure is reduced in the interior of the pouch so as to allow infusion of the liquid into the porous medical implant when the liquid is introduced into the interior of the pouch; and
    a band member conforming to the exterior of the pouch about a circumference of the porous medical implant and capable of forming at least a partial seal between the pouch and the implant.

11. The device of claim 10, wherein the biocompatible material is selected from the group consisting of polylactic acid and polyglycolic acid.

12. The device of claim 11, wherein the biocompatible material has a thickness of between 0.002 and 0.008 of an inch.

13. The device of claim 12, wherein the coupling member is a threaded union.

14. The device of claim 13, wherein the threaded union is a luer lock.

15. The device of claim 10, wherein the device contains a pharmaceutical substance selected from the group consisting of osteoinductive factors, growth factors, nutrients, drugs, antimicrobial agents, calcium containing compounds and blood proteins.

16. The device of claim 15, wherein the porous medical implant is constructed from a porous material selected from the group consisting of calcium phosphate ceramics, porous metals, ceramic polymer composites, human allografts and porous polymers.

17. The device of claim 16, wherein the porous material is a calcium phosphate ceramic.

18. The device of claim 17, wherein the first orifice is closed due to a heat-sealing process.

19. The device of claim 17, wherein the first orifice is closed due to a biocompatible adhesive.

20. The device of claim 17, wherein the first orifice is fitted with a zip-lock mechanism and is closed due to the actuation of the zip-lock mechanism.

\* \* \* \* \*